US00PP25169P3

(12) United States Plant Patent
Olesen

(10) Patent No.: US PP25,169 P3
(45) Date of Patent: Dec. 16, 2014

(54) ***ROSA* HYBRID VARIETY ROSE PLANT NAMED 'POULNAP002'**

(50) Latin Name: ***Rosa* hybrid**
Varietal Denomination: Poulnap002

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/507,034

(22) Filed: May 31, 2012

(65) Prior Publication Data

US 2014/0223617 P1 Aug. 7, 2014

(51) Int. Cl.
*A01H 5/00* (2006.01)

(52) U.S. Cl.
USPC ..... Plt./148

(58) Field of Classification Search
CPC ..... A01H 5/00
USPC ..... Plt./107, 148
See application file for complete search history.

*Primary Examiner* — Anne Grunberg

(57) ABSTRACT

A new garden rose plant of the Floribunda class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulnap002'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2000 and the resulting seeds were planted in a controlled environment in Fredensborg, Denmark. The new variety, named 'Poulnap002', originated as a single seedling from the stated cross.

The new variety may be distinguished from its female seed parent and male pollen parent primarily by flower color. While the claimed plant has flowers which are Red Group 43C, the female seed parent has flowers which are Red Group 36B and Orange Group 29D blend. The male pollen parent has flowers which are Red Group 54D. Furthermore, the male pollen parent is 100 to 150 cm in height, while the claimed plant is about 60 to 100 cm in height.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulnap002' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulnap002' was selected in the spring of 2001 by the inventor as a single plant from the progeny of the aforementioned hybridization.

Asexual reproduction of 'Poulnap002' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulnap002' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap002'.

Specifically illustrated in FIG. 1 are a flower bud, open flowers, petals detached, and reproductive flower parts.

Figure 1:
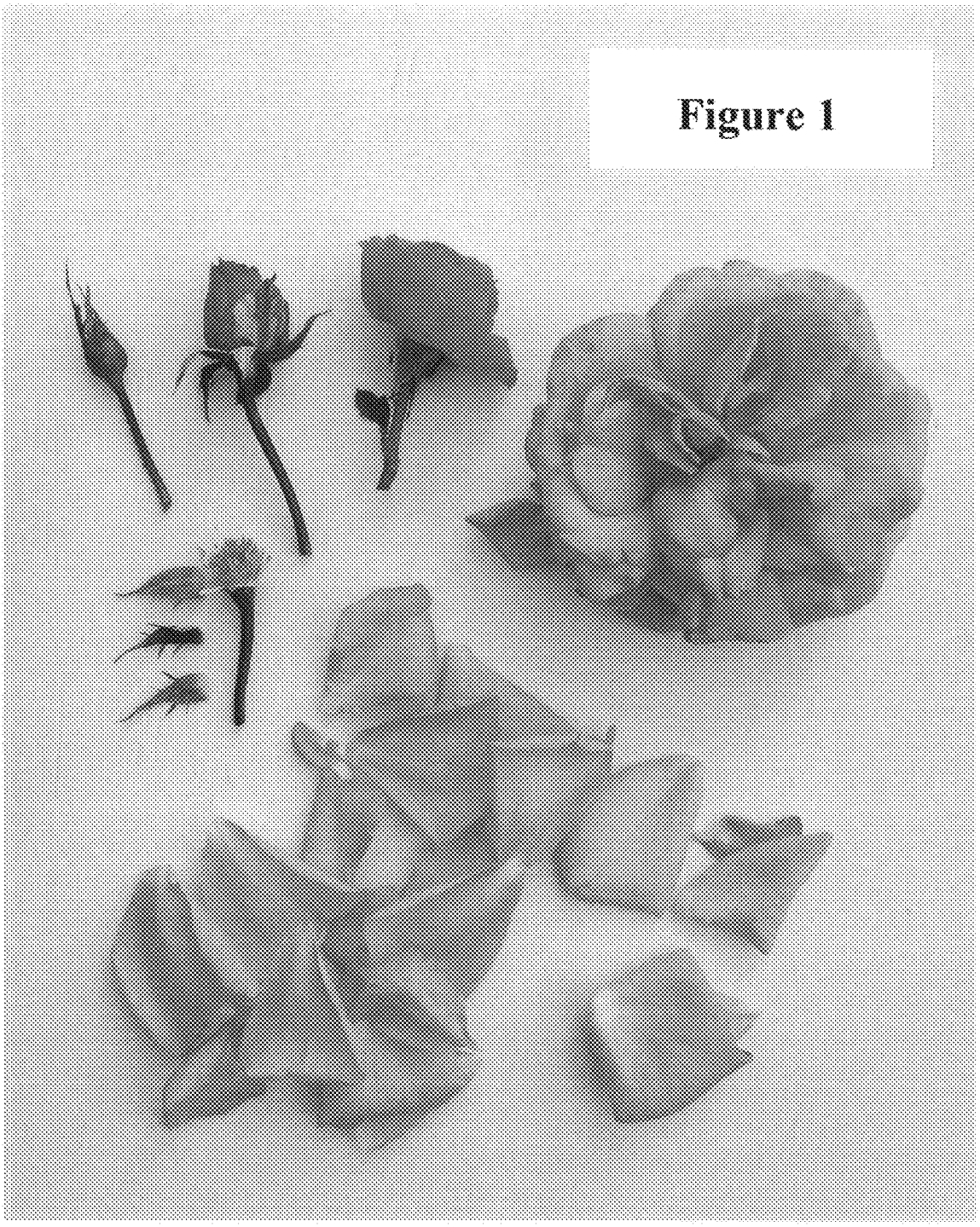
Figure 2:
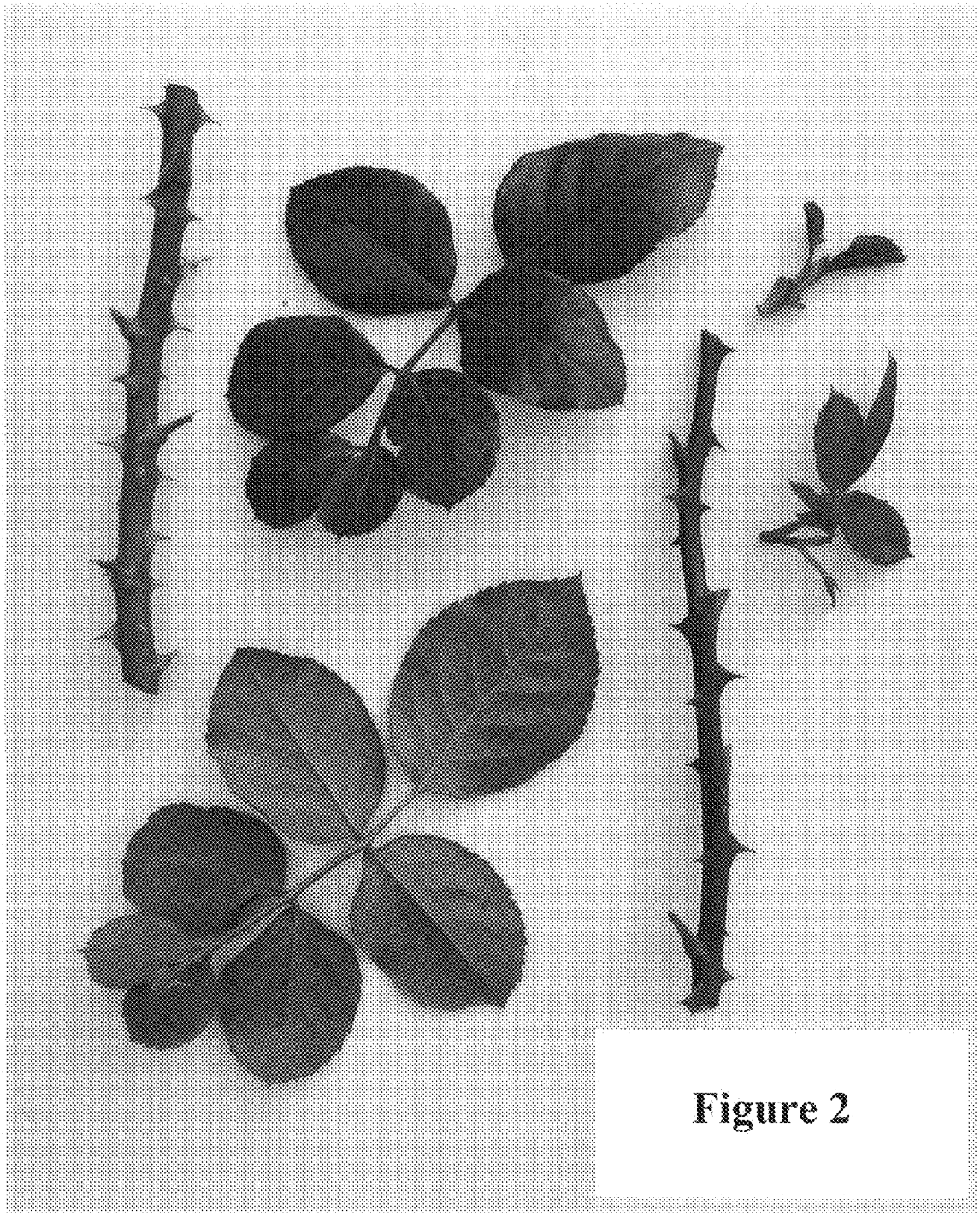

Illustrated in FIG. 2 are mature and juvenile leaves and stems.

DETAILED DESCRIPTION OF THE VARIETY

The following is a description of 'Poulnap002', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulriber', U.S. Plant Pat. No. 12,902 are compared to 'Poulnap002' in Chart 1.

Chart 1

| | 'Poulnap002' | 'Poulriber' |
|---|---|---|
| Petal Count | 50 petals total, 3 of which are petaloids | 18 to 22 |

Chart 1-continued

| | 'Poulnap002' | 'Poulriber' |
|---|---|---|
| Flower Diameter | 120 | 65-75 mm |
| General Tonality of Flower Color | Red Group 43C | Red Group 40C to 41B |

FLOWER AND FLOWER BUD

Blooming habit: Continuous.

Flower bud:

*Size.*—Upon opening, 25 mm in length from base of receptacle to end of bud. Bud diameter is 18 mm.

*Bud form.*—Ovoid.

*Bud color.*—As sepals divide petals are Red Group 52A.

*Sepal inner surface.*—Color: Yellow-Green Group 145B with strong intonations of Greyed-Orange Group 176A. Surface: Smooth with strong pubescence.

*Sepal outer surface.*—Color: Yellow-Green Group 144A with strong intonations of Greyed-Red Group 178A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—35 mm long by 10 mm wide.

*Receptacle.*—Texture: Smooth. Size: 8 mm in height by 10 mm wide. Color: Yellow-Green Group 144A. Anthocyanic pigments the color of Greyed-Red Group 178A. Shape: Campanulate.

*Pedicel.*—Surface: Smooth. Length: 45 to 60 mm. Diameter: 3 to 4 mm. Color: Yellow-Green Group 144A with strong anthocyanic pigments the color of Greyed-Red Group 178A. Strength: Strong.

*Peduncle.*—Length: 5 to 10 cm. Diameter: 4 mm on average. Color: Yellow-Green Group 144A.

Flower bud development: Flower buds are borne singly, and or in clusters of up to 3 flower buds per stem.

Flower bloom:

*Fragrance.*—Strong perfume.

*Duration.*—The blooms have a duration on the plant of approximately 7 to 10 days. Petals fall cleanly away from plant after flowers have fully matured.

*Size.*—Flower diameter is 120 mm when open. Flower depth is 60 mm.

*Flower shape.*—General shape is an open cup with petals that curve out from the center.

*Shape of flower, side view.*—Upon opening the upper portion is a flattened convex. The lower portion is concave.

Petalage: Under normal conditions, flowers have 50 petals total, 3 of which are petaloids.

General tonality of flower: Open flowers are Red Group 43C. Tonality changes to Red Group 48C as the flower ages.

Petal color:

*Upon opening, inner and outer petals.*—Upper surface: Red Group 43C splashed with Orange Group 25D at the middle and basal zone. Lower surface: Red Group 52B splashed with Red Group 49B at the middle zone.

*Basal petal spots, upon opening.*—Upper surface: Yellow Group 4A. Lower surface: Yellow Group 4B.

*After opening, inner and outer petals.*—Upper surface: Red Group 55C. Lower surface: Red-Purple Group 62B.

*Basal petal spots, after opening.*—Upper surface: Yellow Group 4C. Lower surface: Yellow Group 4C.

Petals:

*Petal reflex.*—Somewhat reflexed.

*Margin.*—Entire and uniform. Moderate undulations of margin observed.

*Shape.*—Generally broad and elliptic. Apex shape: Rounded. Base shape: Acute.

*Size.*—65 mm (l)×75 mm (w).

*Texture.*—Smooth.

*Thickness.*—Average.

Petaloids:

*Size.*—30 mm (l) by 11 mm (w).

*Quantity.*—3 on average.

*Shape.*—Asymmetric, generally rounded. The apex is rounded. The base is acute.

*Color.*—Upper surface is Red Group 55C. Lower, Red-Purple Group 62B. Basal petaloid spots, are Yellow Group 4C upper and lower side.

Reproductive organs:

*Pollen.*—None observed.

*Anthers.*—Size: 3 mm in length. Color: Yellow Group 11B. Quantity: 45 on average.

*Filaments.*—Color: Yellow Group 13C and Orange-Red Group 31A. Length: 7 mm.

*Pistils.*—Length: 10 mm. Quantity: 30 on average.

*Stigmas.*—Color: Orange-Red Group 31C.

*Styles.*—Color: Red Group 42C.

*Location of stigmas.*—Superior in location relative to the length of the filaments and the height of the anthers.

*Hips.*—None Observed.

PLANT

Plant growth: Upright, and well branched, floribunda habit. Plants are 60 to 100 cm in height, and 60 cm wide.

Stems:

*Color.*—Juvenile growth: Greyed-Purple Group 183A. Mature growth: Yellow-Green Group 146A.

*Length.*—On average, canes are 50 cm from the base of the plant to the flowering portion.

*Diameter.*—8 mm.

*Internodes.*—On mature canes, there is an average distance of 25 mm between nodes.

*Surface texture.*—Young wood: Smooth. Older wood: Smooth.

Long prickles:

*Incidence.*—15 prickles per 10 cm of stem.

*Size.*—Average length of prickles on mature stems is 7 mm.

*Shape.*—Upper portion is concave. Lower portion is concave.

*Color.*—Juvenile prickles: Greyed-Red Group 178A. Mature prickles: Greyed-Yellow Group 161A.

Plant foliage:

*Compound leaf.*—140 mm (l)×110 (w).

*Quantity.*—4 leaves per 10 cm of stem on average.

*Leaf bearing angle to the stem.*—90 degrees.

*Color of juvenile foliage.*—Upper side: Yellow-Green Group 152C to Yellow-Green Group 146A. Lower side: Yellow-Green Group 146C. Anthocyanin:

Greyed-Red Group 178A on the margins and generalized throughout the leaflets. Color of mature foliage: Upper side: Yellow-Green Group 147A. Lower side: Yellow-Green Group 147C.

Plant leaves and leaflets:

*Stipules*.—Size: 15 mm in length. Quantity: 2 per compound leaf. Shape: Linear, slightly broad based with outward extending apecies. Margins: Finely serrated with few stipitate glands. Color: Yellow-Green Group 144A.

*Petiole*.—Length: 20 mm. Diameter: 3 mm.

*Upper surface*.—Color: Yellow-Green Group 144A. Surface: Stipitate glands.

*Lower surface*.—Color: Yellow-Green Group 144B. Observations: Few small prickles observed.

*Rachis*.—Length: 70 mm.

*Upper surface*.—Color: Yellow-Green Group 144A. Surface: Stipitate glands.

*Lower surface*.—Color: Yellow-Green Group 144B. Observations: Few small prickles observed.

*Leaflet*.—Quantity: Normal number of leaflets leaves in middle of the stem is 7 leaflets. Margins: Serrated. Size: Average size of the terminal leaflet on normal leaves is 65 mm in length by 45 mm wide. Shape: Generally oval. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Floribunda rose class named 'Poulnap002', substantially as illustrated and described herein, due to its abundant pink flowers, disease resistance, and extended period of bloom.

* * * * *